United States Patent [19]

Stanley et al.

[11] 4,378,319

[45] Mar. 29, 1983

[54] PROCESS FOR THE MANUFACTURE OF AROMATIC CYANIDES

[75] Inventors: Robert H. Stanley, Durham, England; Nathan C. Hindley, Lagos, Portugal

[73] Assignee: A. H. Marks & Co., Limited, West Yorkshire, England

[21] Appl. No.: 316,488

[22] Filed: Oct. 29, 1981

[51] Int. Cl.$^3$ .......................................... C07C 121/75
[52] U.S. Cl. .................................................. 260/465 F
[58] Field of Search ..................................... 260/465 F

[56] References Cited

U.S. PATENT DOCUMENTS 3,496,211  2/1970  Dexter et al. ................... 260/465 F
3,983,160  9/1976  Meyer ............................. 260/465 F
4,154,757  5/1979  Cooper et al. ................... 260/465 F
4,301,088 11/1981  Bernhardt ....................... 260/465 F

OTHER PUBLICATIONS

Schwartz et al., J. Org. Chem., 41 (14), 2502–2503 (1976).

Hayashi et al., Bull. Inst. Chem. Res., Kyoto Univ., 52 (3), 514–518 (1974).

Primary Examiner—Dolph H. Torrence

[57] ABSTRACT

The invention provides a process for the preparation of ortho- and para-hydroxybenzyl cyanides. The process of the invention comprises the reaction of an aromatic alcohol selected from ortho- and para-hydroxybenzyl alcohols with a cyanide reagent and an ester capable of esterifying the hydroxyl group of the benzyl alcohol.

In a preferred form of the process there is employed a route via the reaction of an ortho- or para-hydroxybenzyl formate with a cyanide reagent preferably selected from sodium and potassium cyanides.

11 Claims, No Drawings

PROCESS FOR THE MANUFACTURE OF AROMATIC CYANIDES

The invention relates to a process for the preparation of ortho- and para-hydroxybenzyl cyanides optionally substituted in the aromatic nucleus from the corresponding ortho- and para-hydroxybenzyl alcohols.

It is well known that ortho- and para-hydroxybenzyl alcohols, because of the activating influence of the phenol group, cannot be converted in a practical yield into the corresponding benzyl cyanides by halogenation followed by reaction with sodium cyanide in a suitable solvent. However in the case of ortho- and para-hydroxybenzyl alcohol it is possible to achieve the desired conversion under reaction conditions which do not involve the use of acidic reagents. For example para-hydroxybenzyl alcohol may be converted into the corresponding cyanide in 67% yield using a 4% solution of the starting material in dimethyl formamide and heating with sodium cyanide for 20 hours within a temperature range of 110°–130° C. (Schwartz et al., J. Org. Chem. 1976 41 2502-3). Also para-hydroxybenzyl alcohol may first be converted to the corresponding diacetate with acetic anhydride and the diacetate then reacted with potassium cyanide in methanolic solution to give a 70% yield of product (Hayashi et al., Bull. Inst. Chem. Res. Kyoto Univ. 1974 52 514). These reactions have the disadvantage that in the former a large excess of an expensive solvent is used, whilst in the latter the corresponding diacetate must be prepared using an expensive reagent.

Clearly it would be desirable to provide a synthesis which was generally more convenient than the known processes, for example in that it could proceed under mild conditions, could employ readily obtainable reagents and solvents which are relatively less expensive, could give good yields, could employ simplified isolation processes, need not isolate intermediates or the like. A process has now been discovered which can be adapted to offer such advantages.

Accordingly the present invention provides a process for the preparation of an ortho- or para-hydroxybenzyl cyanide which process comprises the reaction of an ortho- or para-hydroxybenzyl alcohol with a cyanide and an ester capable of esterifying the benzyl hydroxyl group.

Esters for use in this invention will normally be primary alcohol aliphatic esters. Apt esters for use in the process of the present invention include acetate and formate esters.

Surprisingly it has been discovered that the use of formate esters offer considerable advantages over the use of acetate esters, for example higher yields may be obtained when using formate esters. Particularly favoured esters for use include methyl formate and ethyl formate.

Suitable cyanides for use in the process of the present invention include the cyanides of the alkali metals. The basic nature of these cyanides is believed to aid the reaction. Preferred cyanides for use in this invention are sodium or potassium cyanide.

The process of the present invention will be carried out in suitable organic solvent. Particular advantages occur if the solvent is a primary alcohol. The most preferred solvents for the process of the invention are methanol and ethanol.

Generally the reaction is carried out at an elevated temperature and is most suitably performed under reflux.

The process may be carried out by mixing together the reactants in the solvent and stirring whilst maintaining the reactants at an elevated temperature. Preferably the temperature is that at which the mixture refluxes.

Under the reaction conditions hydroxyl groups of the ortho- and para-hydroxybenzyl alcohol may be successively esterified by ester transfer involving base catalysed alcoholysis of the ester in the reaction mixture by the solvent. The base catalyst may be the alkali metal cyanides. The following reaction scheme illustrates the process with respect to para-hydroxybenzyl alcohol in the presence of a cyanide such as sodium cyanide and a formate such as methyl formate in a solvent such as methanol.

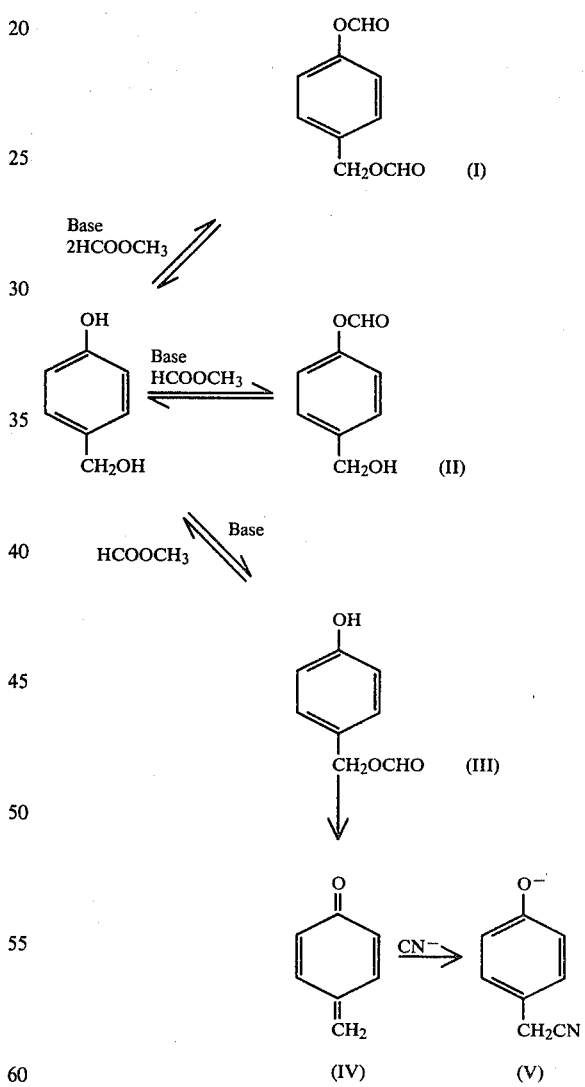

A mixture of the diester (I) and the monoesters (II) and (III) is formed. Only in the case of the monoester (III) with a free phenol function is it possible to generate the reactive quinone methide (IV) which by base catalysis can add cyanide and form the desired product. The reaction system has the advantage that the unreactive esters (I) and (II) may be converted to the reactive ester (III) due to the equilibrium nature of the system. The ester (III) is removed from the system by the irreversible reaction to give compounds (IV) and (V), the unreactive esters may be gradually converted to the reactive ester and may thereby give advantageous yields of the desired product. The use of the formate ester in the reaction is particularly advantageous.

From the aforementioned it is clear that in a further aspect this invention also provides a process for the preparation of ortho- and para-hydroxybenzyl cyanide which comprises the reaction of an ortho- or para-hydroxybenzyl formate with sodium or potassium cyanide.

Suitably this form of the process of this present invention is performed employing a primary alcohol as solvent. Preferably the primary alcohol used in the present invention is methanol or ethanol. Generally this form of the process of the present invention is performed at elevated temperature and is most suitably performed under reflux. Whereas the formate employed in this aspect of the invention may be preformed if desired, most suitably it is formed in situ by transesterification of the hydroxybenzyl alcohol with a formate ester such as methyl or ethyl formate.

The process of this invention is normally carried out in a medium which is a mixture of a primary alcohol and an aliphatic ester. The proportion of primary alcohol to aliphatic ester in the reaction medium is to some extent dictated by the velocity of the reaction. At low or high proportions of primary alcohol to aliphatic ester the reaction velocity may be too slow resulting in the production of unwanted by-products. Suitably the ratio of alcohol to ester is from 1:1 to 4:1 by volume. A preferred mixture would involve 2 to 4 parts alcohol to 1 part ester by volume.

It is preferred that the ester used in the reaction medium is a formate ester and the primary alcohol is methanol or ethanol.

Clearly it is a considerable advantage that the process of this invention may employ relatively inexpensive materials such as methanol, ethanol, methyl-formate and ethyl formate. The use of sodium or potassium cyanides in the process of this invention is also desirable in view of their availability and relatively inexpensive costs.

On completion of a reaction of this invention the excess solvent and reagent are recoverable from the reaction mixture. Suitably this recovery may be carried out using distillation. The reaction products and any unchanged starting material may be separated from inorganic salts by acidification with dilute mineral acid for example sulphuric acid and extraction of the organic material by partition into an organic solvent. Suitable organic solvents include methylene chloride and chloroform. The combined organic extracts may be treated as follows. Firstly the organic solvent is removed by evaporation and the pure product of the process of the present invention isolated by distillation under reduced pressure.

As will be appreciated by the skilled chemist, the process of this invention may also be carried out on ortho- and para-hydroxybenzyl alcohols which are substituted on the aromatic nucleus (provided of course that the substitution is not one which prevents reaction). Suitable substituents include lower alkoxy groups such as the methoxyl group. A hydroxybenzyl alcohol of this type is vanillyl alcohol.

The following Examples illustrate the invention.

EXAMPLE 1

Preparation of para-hydroxybenzyl cyanide

A mixture of 4.96 para-hydroxybenzyl alcohol 2.8 g. sodium cyanide 18 ml. methanol and 6 ml. of methyl formate is heated with stirring under reflux for a period of 70 minutes. The reaction mixture is distilled under partial vacuum to recover starting material, and the residue stirred with 20 ml. water and sulphuric acid added until the mixture is no longer alkaline. The product is now isolated by extracting 3 times each time with 15 ml. methylene chloride. The combined solvent extracts are washed with 10 ml. aqueous sodium bicarbonate and solvent evaporated finally under vacuum at a temperature of 60° C. There is obtained 5.11 g. of crude para-hydroxybenzyl cyanide corresponding to a weight yield of 96% of theory. On simple distillation under oil pump vacuum there is obtained a pale yellow fraction m.pt. 65° C. corresponding to a weight yield equivalent to 93% of theory. Melting point data indicates that this material has an absolute purity of 97%.

EXAMPLE 2

Preparation of para-hydroxybenzyl cyanide

A mixture of 4.96 g. para-hydroxybenzyl alcohol 2.4 g. sodium cyanide 12 ml. ethanol and 12 ml. ethyl formate is heated with stirring under reflux for a period of ninety minutes. The reaction product is then subjected to the same isolation process as in Example 1 to give a 94% yield of crude product showing a melting point of 58°-61° C. uncorrected.

EXAMPLE 3

Preparation of para-hydroxybenzyl cyanide

A reaction was carried out in an analogous manner to Example 1 except that methyl acetate was used in place of methyl formate. Para-hydroxybenzyl cyanide was obtained in a less advantageous yield than in Example 1.

EXAMPLE 4

Preparation of ortho-hydroxybenzyl cyanide

A reaction was carried out in an analgous manner to Example 1 except that ortho-hydroxybenzyl alcohol was used in place of para-hydroxybenzyl alcohol. Ortho-hydroxybenzyl cyanide was obtained in a yield of 92.7%. (Crude product)

EXAMPLE 5

Preparation of 4-hydroxy-3-methoxy benzyl cyanide

A reaction was carried out in an analogous manner to Example 1 except that 4-hydroxy-3-methoxy benzyl alcohol was used in place of para-hydroxybenzyl alcohol. 4-Hydroxy-3-methoxybenzyl cyanide was obtained in a yield of 77.4%. (Crude product).

We claim:
1. A process for the preparation of ortho- and/or para-hydroxybenzyl cyanide which consists essentially in reacting the corresponding ortho- or para-hydroxybenzyl alcohol with a cyanide reagent and an ester capable of esterifying said alcohol and in the further presence of a solvent selected from the class of methanol and ethanol, and recovering the corresponding hydroxybenzyl cyanide from the reaction mixture.

2. A process according to claim 1, wherein the cyanide reagent is selected from sodium and potassium cyanides.

3. A process according to claim 1, wherein the ester is a primary alcohol aliphatic ester.

4. A process according to claim 1, wherein the ester is a formate.

5. A process according to claim 4, wherein the formate is selected from methyl formate and ethyl formate.

6. A process according to claim 1, wherein the reaction is carried out at an elevated temperature.

7. A process according to claim 1, wherein the reaction is carried out under reflux.

8. A process according to claim 7 or claim 1, wherein the ratio of alcohol to ester is from about 1:1 to about 4:1 by volume.

9. A process for the preparation of an aromatic cyanide selected from ortho- and para-hydroxybenzyl cyanides, which process comprises reacting:
(a) a cyanide reagent selected from sodium and potassium cyanides with,
(b) an aromatic starting material selected from (i) ortho- and para-hydroxybenzyl alcohols together with a formate ester, and (ii) ortho- and para-hydroxybenzyl formates alone,
in a primary alcohol solvent selected from methanol and ethanol, at about reflux temperature with a ratio of alcohol to ester of from about 2:1 to about 4:1 by volume to produce the said aromatic cyanide.

10. A process according to claim 9, wherein excess solvent and reactants are recovered after reaction by distillation, and after removal of excess solvent and reactants the product is separated from inorganic salts via extraction into an organic solvent from an acidic aqueous medium, and the pure product is obtained by evaporating the organic solvent and distilling the product under reduced pressure.

11. A process which comprises reacting an ortho- or para-hydroxybenzyl formate ester with sodium or potassium cyanide in the presence of methanol or ethanol as reaction solvent to produce, respectively, an ortho- or para-hydroxybenzyl cyanide.

* * * * *